United States Patent

Nickel et al.

[11] Patent Number: 4,839,468
[45] Date of Patent: Jun. 13, 1989

[54] N-(HYDROXY-SULPHO-NAPHTHYAMINO-TRIAZINYL)-ARYLENE-DIAMINES

[75] Inventors: Horst Nickel, Leverkusen; Peter Wild, Alten Buseck; Frank-Michael Stöhr, Burscheid, all of Fed. Rep. of Germany

[73] Assignee: Bayer Aktiengesellschaft, Leverkusen, Fed. Rep. of Germany

[21] Appl. No.: 670,683

[22] Filed: Nov. 13, 1984

Related U.S. Application Data

[63] Continuation of Ser. No. 607,332, May 4, 1984, abandoned, which is a continuation-in-part of Ser. No. 360,288, Mar. 22, 1982, abandoned.

[30] Foreign Application Priority Data

Apr. 8, 1981 [DE] Fed. Rep. of Germany ....... 3114087

[51] Int. Cl.$^4$ ..................... C09B 44/00; C09B 44/08; C09B 62/00; D06P 1/41
[52] U.S. Cl. .................................... 534/604; 534/605; 534/614; 534/797; 534/803; 534/632; 534/635; 534/636; 534/637; 534/638; 534/642; 534/589
[58] Field of Search ............................. 260/146 T, 163; 534/632, 635, 636, 637, 638, 604, 605, 614, 603, 797, 803

[56] References Cited

U.S. PATENT DOCUMENTS 3,206,451  9/1965  Benz et al. ........................ 260/153
4,083,847  4/1978  Koller et al. ..................... 260/199 X
4,333,874  6/1982  Nickel et al. ..................... 260/153
4,363,761  12/1982  Pedrazzi, I ........................ 260/153

FOREIGN PATENT DOCUMENTS 0022209  1/1981  European Pat. Off. ............ 260/153
951667   3/1964  United Kingdom ............... 260/153
2019873  11/1979 United Kingdom ............... 260/153

Primary Examiner—Floyd D. Higel
Attorney, Agent, or Firm—Sprung Horn Kramer & Woods

[57] ABSTRACT

Triazine compounds which in their betaine form correspond to the formula

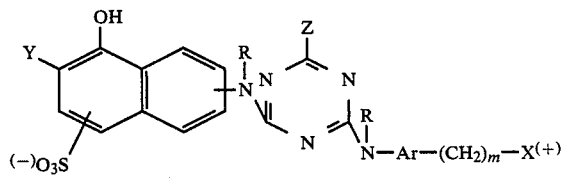

wherein
Y denotes hydrogen or the radical of an azo dye-stuff,
R denotes hydrogen or alkyl,
Ar denotes arylene,
Z denotes halogen, hydroxyl, alkoxy, alkyl, aryl or an amino group which may be monosubstituted or disubstituted,
m denotes 0 or 1 and
$X^{(+)}$ denotes an ammonium group amd wherein
the cyclic and acyclic radicals can carry further substituents, are used for dyeing/coloring natural and synthetic substrates and compositions, in particular paper.

16 Claims, No Drawings

N-(HYDROXY-SULPHO-NAPHTHYAMINO-TRIAZINYL)-ARYLENE-DIAMINES

This application is a continuation of patent application Ser. No. 607,332, filed May 4, 1984, now pending, which in turn is a continuation-in-part application of patent application Ser. No. 360,288, filed Mar. 22, 1982, now abandoned.

The invention relates to water-soluble triazine compounds which in their betaine form correspond to the formula

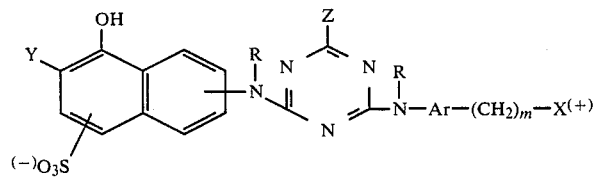

wherein
Y denotes hydrogen or the radical of an azo dye-stuff,
R denotes hydrogen or alkyl, in particular methyl,
Ar denotes arylene,
Z denotes halogen, hydroxyl, alkoxy, alkyl, aryl or an amino group which may be monosubstituted or disubstituted,
m denotes 0 or 1 and
$X^{(+)}$ *denotes an ammonium group*
and wherein
the cyclic and acyclic radicals can carry further substitutents,
to their preparation and—when Y represents the radical of an azo dyestuff—to their use for dyeing/colouring synthetic and natural materials, in particular paper, and also—when Y denotes hydrogen—to their use as coupling components for the preparation of azo dyestuffs.

Those dyestuffs of the formula (I) are preferred wherein R represents hydrogen and the sulphonic acid group is in the 3-position.

The ammonium group $X^{(+)}$ is understood as meaning in particular a group of the formula wherein
$R_1$, $R_2$ and $R_3$ independently of one another denote hydrogen, $C_1$- to $C_4$-alkyl, $C_3$- or $C_4$-alkenyl, benzyl or phenylethyl, which can be substituted by hydroxyl, $C_1$- to $C_4$-alkoxy, halogen or cyano and the benzyl radical and phenylethyl radical can additionally be substituted by $C_1$- to $C_4$-alkyl, or $R_2$ or $R_3$ together with the nitrogen atom to which they are bonded denote a 5- or 6-membered ring.

Those water-soluble, cationic azo dyestuffs are emphasised which have the formulae

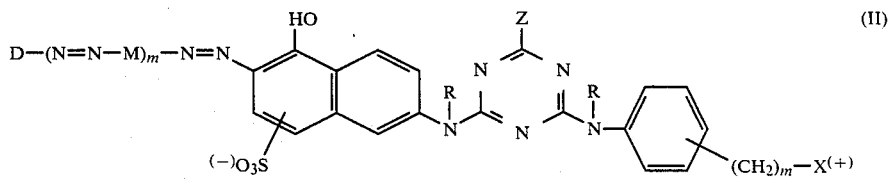

wherein
D denotes the radical of a diazo component of the benzene, naphthalene or heterocyclic series,
M denotes the radical of a coupling component of the benzene or naphthalene series, and
m, R, $X^{(+)}$ and Z have the above meaning,
and wherein
the total number of basic and cationic groups is at least 2, and

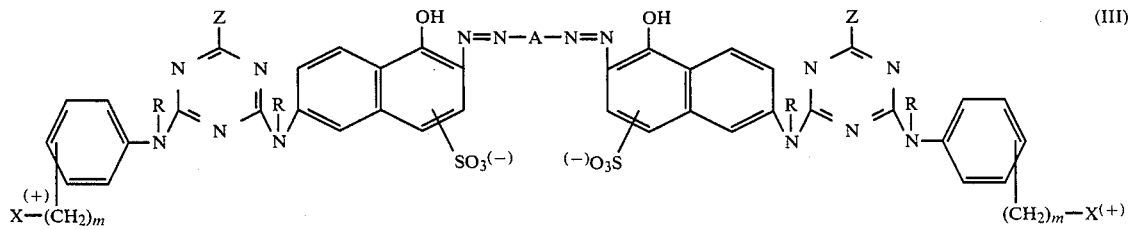

wherein
A represents the radical of an aromatic tetraazo component
and wherein
the total number of basic and cationic groups in the molecule must be greater than 2.

In order to make the dyestuffs water-soluble, it is necessary that the total number of basic and cationic groups is larger than the number of sulphonic acid groups, since each sulphonic acid group can form an inner, sparingly soluble salt with, in each case, one basic or cationic group.

This (these) additional basic or cationic group(s) can be situated in D, M, A and Z.

Halogen represents in particular fluorine, chlorine or bromine.

Preferably, alkyl represents $C_1$-$C_4$-alkyl, alkoxy represents $C_1$-$C_4$-alkoxy, arylene represents phenylene or naphthylene and aryl represents phenyl or naphthyl, which may be substituted by halogen, $C_1$-$C_4$-alkyl or $C_1$-$C_4$-alkoxy.

A preferred amino group Z has the formula $$\left( \begin{array}{c} R_4 \\ | \\ -N-(CH_2)_n \end{array} \right)_o -N\begin{array}{c} R_2 \\ \diagup \\ \diagdown \\ R_4 \end{array} \quad \text{or} \quad -N\begin{array}{c} R_4 \\ | \\ \end{array}\!\!\bigcirc\!\!\begin{array}{c} R_2 \\ \diagup \\ N \\ \diagdown \\ R_4 \end{array}$$

(IV)                  (V)

wherein n represents 2 or 3 and, in addition, O when o denotes 1, o represents 0, 1 and $R_4$ represents $R_3$ and, in addition, naphthyl or phenyl which may be substituted by halogen, $C_1$-$C_4$-alkyl, hydroxyl, $C_1$-$C_4$-alkoxy or the radicals $$(CH_2)_m-N\begin{array}{c} R_2 \\ \diagup \\ \diagdown \\ R_3 \end{array} \quad (CH_2)_m-\overset{(+)}{N}\begin{array}{c} R_1 \\ \diagup \\ \diagdown R_2 \\ R_3 \end{array} A^{(-)}$$

(VI)                 (VII)

or $$\begin{array}{c} R_5 \\ \diagdown \end{array}\!\!\!\begin{array}{c} S \\ \diagup \\ \diagdown \\ N \end{array}\!\!\!\!\!\!\!\!\!$$

(VIII)

2-benzothiazolyl or 3-isobenzothiazolyl, $R_5$ represents hydrogen, $C_1$-$C_4$-alkyl, $C_1$-$C_4$-alkoxy or halogen, $A^{(-)}$ represents an anion and m, $R_1$, $R_2$ and $R_3$ have the abovementioned meaning.

D and M preferably represent a radical of the benzene or naphthalene series. Particularly suitable substitutents on these rings are $C_1$-$C_4$-alkyl, hydroxyl, $C_1$-$C_4$-alkoxy, halogen, the sulphonic acid group, the groups (VI)-(VIII) and a group of the formula $$Z\begin{array}{c} \diagup \\ \end{array}\!\!N\!\!\begin{array}{c} \diagdown \\ \end{array}Z \quad (IX)$$
$$N\!\!\begin{array}{c} \diagdown \\ \diagup \end{array}\!\!N$$
$$NH-$$

NH—CO—$CH_3$ and $NHCOC_6H_5$.

Preferred radicals A are 1,4- or 1,3-phenylene which may be substituted by $C_1$-$C_4$-alkyl, hydroxyl, $C_1$-$C_4$-alkoxy or halogen or a radical of the formula $$\begin{array}{c} R_5 \\ \end{array}\!\!\!\bigcirc\!\!-R_6-\!\!\bigcirc\!\!\!\begin{array}{c} R_5 \\ \end{array} \quad (X)$$

in which $R_6$ denotes a direct bond, —$(CH_2)_p$—, —O—, —O—$(CH_2)_p$—O—, —$SO_2$—, —NH—CO—, —NH—CO—NH—, —NH—CO—$(CH_2)_p$—CO—NH—, —CO—NH—$(CH_2)_p$—NH—CO— or $$Z\begin{array}{c} \diagup \\ \end{array}\!\!N\!\!\begin{array}{c} \diagdown \\ \end{array}NH- \quad (XI)$$
$$N\!\!\begin{array}{c} \diagdown \\ \diagup \end{array}\!\!N$$
$$NH-$$

and p denotes 1, 2 or 3.

Diazo or tetraazo components must be so chosen that the condition of water-solubility is satisfied, that is to say that the resulting dyestuff molecule contains at least one basic or cationic group more than sulphonic acid groups contained in the molecule.

Thus, if the coupling component I (Y denoting hydrogen) has in addition to the cationic group $X^{\oplus}$ a second basic or cationic group in Z, an aromatic carbocyclic or hetrocyclic diazo or tetraazo component-which is free from anionic groups-such as, for example, aniline, aminoazobenzene, aminonaphthalene, 4,4'-diaminobenzoylanilide, 4,4'-diamino-3,3'-dimethyldiphenyl, 4,4'-diamino-3,3'-dimethoxydiphenyl or 4,4'-diaminodiphenyl-1,2-ethane, can be used.

If, on the other hand, the coupling component I (Y denoting hydrogen) has only the cationic group $X^{\oplus}$, the aromatic carbocyclic or heterocyclic diazo or tetraazo component must contain at least one basic or cationic group in order to achieve solubility in water.

Examples of suitable diazo components of this type are aniline-3- or -4-trimethylammonium chloride, aniline-3- or -4-trimethylammonium sulphate, aniline-3- or -4-trimethylammonium methosulphate, aniline-3- or -4-trimethylammonium tosylate, aniline-3- or -4-trimethylammonium benzenesulphonate, 3- or 4-aminobenzyldimethylammonium chloride, 3- or 4-aminobenzyltrimethylammonium chloride, 3- or 4-aminobenzyldimethylammonium methosulphate, 3- or 4-aminobenzyltrimethylammonium methosulphate or 2-aminonaphthalene-5-methylene trimethylammonium methosulphate.

Among these are also aminoazo compounds which may have ammonium groups bonded via a methylene group, such as 4-aminoazobenzene-4'-dimethylammonium chloride, 4-aminoazobenzene-4'-trimethylammonium chloride, 4-aminoazobenzene-3'-trimethylammonium chloride, 4-aminoazobenzene-4'- or -3'-methylenetrimethylammonium chloride and compounds which are substituted in the 3- or 2-position in the benzene nucleus of these azobenzenes by methyl, methoxy, ethoxy or chlorine, such as 2-aminonaphthalene-5-methylenetrimethylammonium chloride→aniline or →3-methylaniline or →2-methoxyaniline.

Coupling components I (Y denoting H) are prepared in a known manner in general as follows: a naphthalene-sulphonic acid (XII), preferably a -3-sulphonic acid, is first reacted with a cyanuric halide, preferably the chloride or fluoride, to give a 1:1 compound. A Z-substituent is then introduced by replacing the halogen, for example with the aid of ammonia or amines HZ.

After the substituent Z has been introduced in the second stage (at 20°–50° C.) a condensation is carried out with the amino compound (XIII) in the third stage at 70°–95° C.

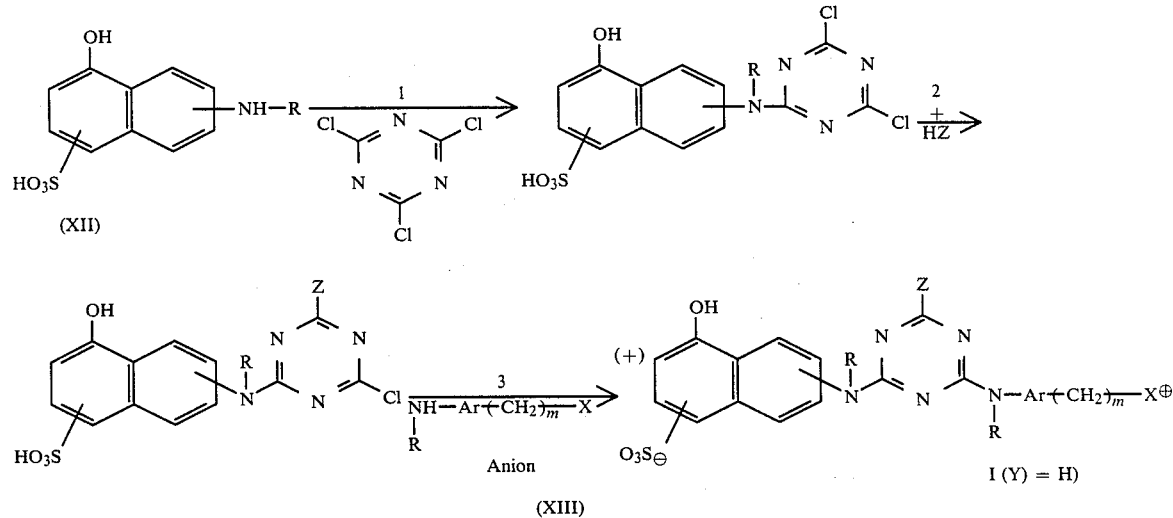

If Z denotes F, Cl or Br, the aromatic amino compound (XIII) carrying the ammonium group is condensed in the second stage.

Individual condensation stteps can of course be interchanged and, for example, the amino compound (XIII) can first be condensed with a cyanuric halide.

Examples which may be mentioned of compounds HZ are $C_1$–$C_4$-monoalkylamines or $C_1$–$C_4$-dialkylamines, such as methylamine, ethylamine, chloroethylamine, propylamine, isopropylamine, butylamine, hydroxyethylamine, 2-methoxyethylamine, dimethylamine, diethylamine, di-i-propylamine, di-n-propylamine, diethanolamine, diisopropanolamine, diisobutylamine, methylethylamine, methylethanolamine, ethylethanolamine and 3-methylaminopropane nitrile, cycloalkylamines, such as piperidine, morpholine, piperazine, methylpiperazine and hydroxyethylpiperazine aralkylamines such as benzylamine benzylmethylamine or benzylethanolamine, which can be substituted by chlorine or methyl in the phenyl nucleus, diamines, such as ethylenediamine, N,N'-dimethylethylenediamine, 1-amino-2-diethylaminoethane, propylenediamine, N-methylpropylenediamine, N,N-dimethylpropylenediamine, N,N-diethylpropylenediamine, dipropylenetriamine, diethylenetriamine, N,N',N''-trimethyldiethylenetriamine or 1,4-diaminocyclohexane, aromatic amines, such as aniline, N-methylaniline, ethylaniline or hydroxyethylaniline, which can be substituted in the phenyl nucleus in the o-, m- or p-position by methyl, ethyl, chlorine, methoxy, ethoxy, N,N-dimethylamino, N,N-diethylamino, trimethylammonium chloride, trimethylammonium methosulphate, trimethylammonium acetate, methylenedimethylamino or methylenetrimethylammonium methosulphate, 1-naphthylamine, dehydrothiootoluidine, dehydrothioxylidine, 2-aminobenzothiazole, 3-aminoisobenzothiazole, 2-aminonaphthalene-5-methylenetrimethylammonium chloride and also methylhydrazine and dimethylhydrazine.

New azo dyestuffs I(Y denoting the radical of an azo dyestuff) are prepared by customary processes known in azo chemistry (see, for example, Houben-Weyl, Methoden der organischen Chemie (Methods of Organic Chemistry), volume X/3, Georg Thieme Verlag Stuttgart 1965, from page 226 and page 270) by azo coupling diazonium or tetrazonium compounds with coupling components of the formula I (Y denoting H), preferably in an aqueous medium.

If Z denotes alkyl or aryl, there are of course only 2 replaceable halogne substituents available in the triazine ring, it being optional whether (XIII) or the aminonaphtholsulphonic acid is condensed first.

Examples of suitable amino compounds (XIII) are (with the anion $A^{(-)}$ preferably being chloride, bromide, methosulphate, tosylate or benzenesulphonate)

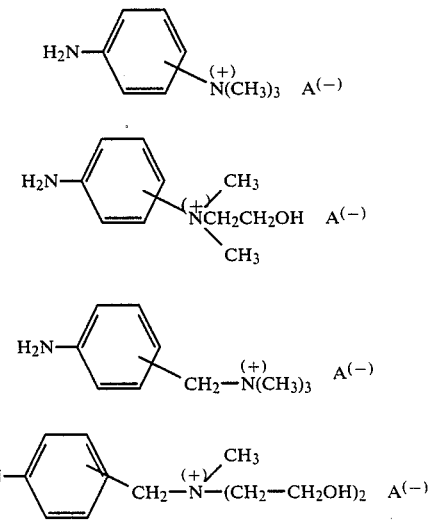

-continued

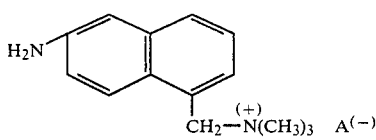

The dyestuffs are used for dyeing/colouring materials which can be dyed/coloured with cationic dyestuffs. Examples which may be mentioned are polyacrylonitrile, acid-modified polyesters, for example polyglycol terephthalates, as described in Belgian Patent Specification No. 549,179 or U.S. Pat. Specification No. 2,893,816, acid-modified polyamides, tanninmordanted vegetable fibers (cotton), leather and, preferably, paper. The dyestuffs are suitable for colouring sized and unsized paper, it being possible to use either bleached or unbleached pulp as the starting material and to use hardwood pulp or softwood pulp, such as birch and/or pine sulphite and/or sulphate pulp.

The dyestuffs are used not only as powder or granular formulations but also in the form of concentrated solutions. Powder formulations are standardised in a customary manner with standardising substances, such as sodium sulphate, sodium phosphate, sodium chloride or sodium acetate, in the presence of dedusting agents, or the dyestuffs are marketed directly as spray-dried formulations. Concentrated dyestuff solutions can be of an aqueous or aqueous-organic type, customary, environmentally acceptable and, as far as possible, readily degradable additives being preferred, such as organic acids, preferably acetic acid or formic acid, amides, such as formamide, dimethylformamide or urea, or alcohols such as glycol, diehylene glycol or diethylene glycol ethers, preferably its methyl ether or ethyl ether.

The dyestuffs have an excellent affinity and very good general fastness properties. Colourings of paper are distinguished by very good wet-fastness properties and also fastness to alum, acid and alkali. They have a surprisingly high light-fastness and, at the same time, a high clarity and intensity.

Numbers identified in the examples by "Index No." are hue indications according to the "Colour Index Hue Indication Chart".

EXAMPLE 1

18.5 parts (0.1 mol) of cyanuric chloride, dissolved in 200 parts of acetone, are suspended in 300 parts of ice water. An aqueous solution of 18.6 parts (0.1 mol) of aniline-3-trimethylammonium chloride (about 70 parts by volume) is added as the 1st condensation component to the suspension at 0° to 5° C. and the mixture is stirred until the first condensation is complete (about ½ hour), pH being maintained at 4-5 and the acid being liberated being neutralised by means of a 20% strength sodium carbonate solution. The condensation product has precipitated.

A solution of 18 parts of aniline-3-trimethylammonium chloride (about 70 parts by volume) is then added as the 2nd condensation component, the mixture is heated to 40°-50° C., the pH value is maintained at 5-6 by the dropwise addition of 20% strength sodium carbonate solution and the mixture is stirred until the ammonium compound is no longer detectable (test by diazotising and coupling to an R salt solution). The resulting monochloro compound is present in the form of a solution after the condensation reaction is complete. A solution of 21 parts of 6-amino-1-hydroxynaphthalene-3-sulphonic acid (J acid) in 200 parts of water (pH about 6) is then added as the 3rd condensation component, the mixture is heated to 80°-90° C. and liberated acid is neutralised by means of a 20% strength sodium carbonate solution by maintaining the pH at about 6.

After the third condensation is complete, the resulting coupling component has the formula

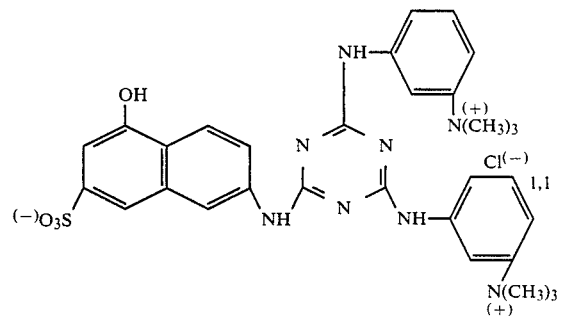

and its pH is adjusted to 2 by acidification with 28% strength hydrochloric acid and it can be further processed directly in this acid/salt form or it can be isolated in a customary manner, for example as a zinc double salt.

If J acid is used as the first condensation component and the condensation reaction is carried out as above at 0° to 5° C. with cyanuric chloride, then an intermediate isolation is advantageously carried out after the 2nd condensation stage at 40°-50° C. with aniline or N-methylaniline, 2-methylaniline, methylamine, dimethylamine, N,N-dimethylpropylenediamine or other amines HZ indicated above and the condensation reaction is finally carried out in the third stage at 80°-95° C. with aniline-3-trimethylammonium chloride or aniline-3-trimethylammonium acetate, for example to give the coupling component

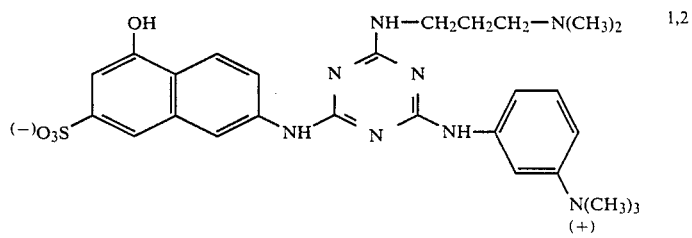

If in the third stage a condensation reaction is carried out with 3- or 4-aminobenzyltrimethylammonium chloride, for example the coupling component

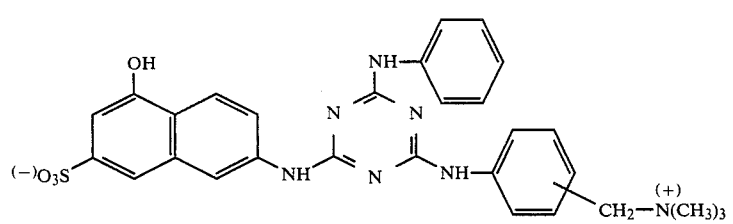
1,3
is thus obtained.
Further coupling components (I) (Y denoting H) are listed in the table below.
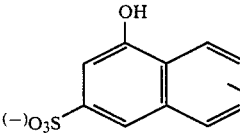
| | Acid | HZ | $H_2N-Ar-(CH_2)_m-X^{(+)}$ |
|---|---|---|---|
| 1,4 | J acid | Aniline | 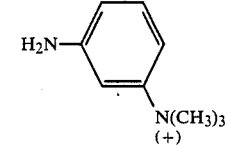 |
| 1,5 | J acid | N—Methylaniline | 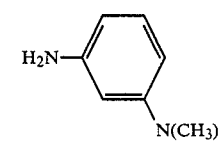 |
| 1,6 | J acid | Methylamine | 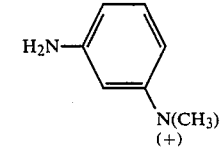 |
| 1,7 | J acid | Dimethylamine | 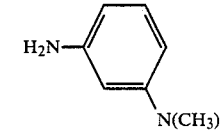 |
| 1,8 | J acid | Diethanolamine | 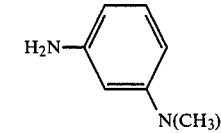 |
| 1,9 | J acid | Diisopropanolamine | 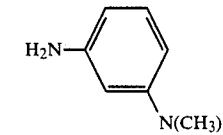 |

-continued

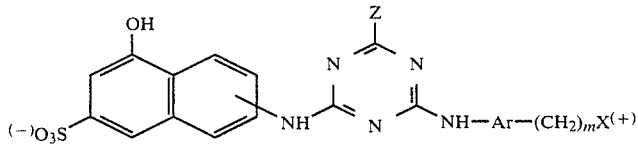

| Acid | HZ | $H_2N-Ar-(CH_2)_m-X^{(+)}$ |
|---|---|---|
| 1,10 J acid | Morpholine | 3-$H_2N$-C$_6$H$_4$-N(CH$_3$)$_3^{(+)}$ (meta) |
| 1,11 J acid | Piperidine | 3-$H_2N$-C$_6$H$_4$-N(CH$_3$)$_3^{(+)}$ (meta) |
| 1,12 J acid | Piperazine | 3-$H_2N$-C$_6$H$_4$-N(CH$_3$)$_3^{(+)}$ (meta) |
| 1,13 J acid | N—Me—piperazine | 3-$H_2N$-C$_6$H$_4$-N(CH$_3$)$_3^{(+)}$ (meta) |
| 1,14 J acid | H—Hydroxyethylpiperazine | 3-$H_2N$-C$_6$H$_4$-N(CH$_3$)$_3^{(+)}$ (meta) |
| 1,15 J acid | Ammonia | 3-$H_2N$-C$_6$H$_4$-N(CH$_3$)$_3^{(+)}$ (meta) |
| 1,16 J acid | Ethylenediamine | 3-$H_2N$-C$_6$H$_4$-N(CH$_3$)$_3^{(+)}$ (meta) |
| 1,17 J acid | Dimethylamine | 4-$H_2N$-C$_6$H$_4$-N(CH$_3$)$_3^{(+)}$ (para) |
| 1,18 J acid | Diethanolamine | 4-$H_2N$-C$_6$H$_4$-N(CH$_3$)$_3^{(+)}$ (para) |

-continued

| | Acid | HZ | $H_2N-Ar-(CH_2)_m-X^{(+)}$ |
|---|---|---|---|
| 1,19 | J acid | Diethanolamine | 6-aminonaphthalene with $CH_2-N(CH_3)_3^{(+)}$ |
| 1,20 | J acid | Diisopropanolamine | 6-aminonaphthalene with $CH_2-N(CH_3)_3^{(+)}$ |
| 1,21 | J acid | Ammonia | 6-aminonaphthalene with $CH_2-N(CH_3)_3^{(+)}$ |
| 1,22 | J acid | Ammonia | $H_2N$-phenyl-$CH_2-N^{(+)}(CH_3)_2(CH_2CH_2OH)$ |
| 1,23 | J acid | Diethanolamine | $H_2N$-phenyl-$CH_2-N^{(+)}(CH_3)_2(CH_2CH_2OH)$ |
| 1,24 | J acid | Diethanolamine | $H_2N$-phenyl-$N^{(+)}(CH_2-CH_2OH)_3$ |
| 1,25 | Methyl-J acid | Dimethylpropylenediamine | $H_2N$-phenyl-$N(CH_3)_3^{(+)}$ (meta) |
| 1,26 | Gamma acid | Dimethylamine | $H_2N$-phenyl-$N(CH_3)_3^{(+)}$ (meta) |
| 1,27 | Gamma acid | Diethanolamine | $H_2N$-phenyl-$N(CH_3)_3^{(+)}$ (meta) |
| 1,28 | Gamma acid | Dimethylpropylenediamine | $H_2N$-phenyl-$N(CH_3)_3^{(+)}$ (meta) |

-continued

| | | | |
|---|---|---|---|
| | OH | Z | |
| | (naphthalene with $(^-)O_3S$ and $NH-C(=N)-N=C(-NH-Ar-(CH_2)_m-X^{(+)})-Z$ triazine) | | |
| | Acid | HZ | $H_2N-Ar-(CH_2)_m-X^{(+)}$ |
| 1,29 | Gamma acid | 4-Acetylaminoaniline | $H_2N-C_6H_4-N(CH_3)_3^{(+)}$ (meta) |
| 1,30 | J acid | Aminoethylpiperazine | $H_2N-C_6H_4-N(CH_3)_3^{(+)}$ (meta) |
| 1,31 | J acid | Aminoethylpiperazine | $H_2N-C_6H_4-N(CH_3)_3^{(\oplus)}$ (para) |

EXAMPLE 2

A hydrochloric acid solution of 25 parts (0.1 mol) of 2-aminonaphthalene-5-methylenetrimethylammonium chloride (about 70 parts by volume) is diazotised in a customary manner at 0° C. after the addition of about 100 parts of ice by means of 24 parts of a 30% strength aqueous sodium nitrite solution. The diazonium salt remains in solution. Shortly before the coupling, excess nitrous acid is destroyed with amidosulphonic acid.

60.7 parts (0.1 mol) of the coupling component 1,5 of the formula

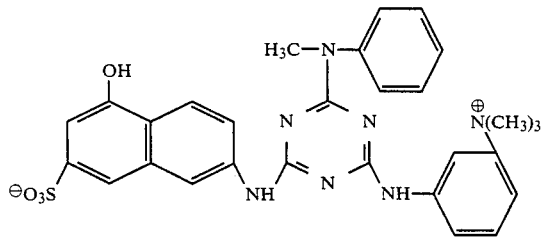

are dissolved in 700 parts of an aqueous sodium hydroxide solution and the pH is adjusted to 4.5 by means of 50% strength acetic acid, which causes the compound to precipitate. The mixture is cooled down to 5° C. and the ice-cold diazonium salt solution is then added. The pH is adjusted to 4-5 by the dropwise addition of a sodium acetate solution (20% strength) and the mixture is stirred overnight until the coupling is complete, during which time the dyestuff precipitates.

The precipitated dyestuff is isolated and dried. After drying, it is a dark powder which gives a red solution in water.

To prepare a dyestuff solution the precipitated dyestuff of the coupling batch is adjusted to pH 12 by means of a 40% strength sodium hydroxide solution, the dyestuff is isolated and the dyestuff paste obtained is dissolved at about 50° C. in 120 parts of 50% strength acetic acid and cleared of slight residues.

The cold-stable red dyestuff solution obtained colours paper by the customry colouring processes (with or without the addition of size) in intense red hues (Index No. 7). The dyestuff has good wet-fastness properties.

If instead of the above 2-aminonaphthaleneammonium compound, an equimolar amount of aniline-3-trimethylammonium chloride or aniline-4-trimethylammonium chloride is used as the diazo component, orange-coloured dyestuffs or dyestuff solutions are obtained (Index No. 5). With 3- or 4-aminobenzyltrimethylammonium chloride as the diazo component, likewise orange-coloured colourings of paper are obtained (Index No. 5). 4-Aminoazobenzene-4'-trimethylammonium chloride as the diazo component produces a bluish-tinged red dyestuff (Index No. 10). If the coupling component used is not the above compound 1,5 but the coupling components 1,2 or 1,3, 1,8, 1,9, 1,10, 1,11, 1,14, 1,15, 1,19, 1,20, 1,27, 1,28, 1,30 or 1,31, the above diazo components produce dyestuffs which colour paper in similar hues as are obtained with the above coupling component 1,5.

EXAMPLE 3

A hydrochloric acid solution of 0.1 mol of the coupling component of the formula 1,1 (500 parts by volume) is cooled down to 0° with ice and combined with a solution which has been prepared in a customary manner of 0.1 mol of 4-chlorobenzenediazonium chloride (230 parts by volume). A 20% strength sodium acetate solution is then added dropwise until the pH has risen to 4-5 and the mixture is stirred until the coupling is complete. The dyestuff of the formula

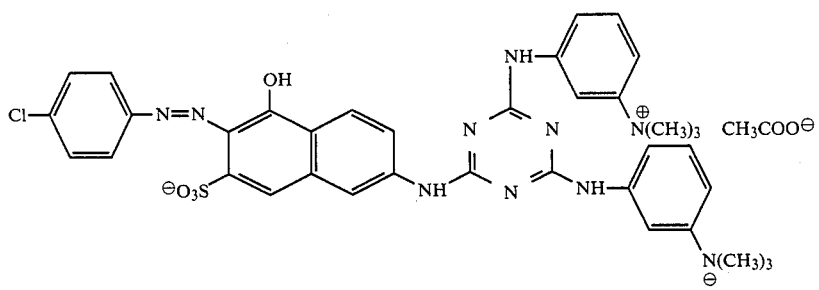

is isolated in a customary manner and either it is dried or a dyestuff solution is prepared by means of 50% strength acetic acid. The dyestuff colours paper in orange-coloured hues (Index No. 6).

If instead of using 4-chloroaniline as the diazo component, aniline, 4-aminotoluene, 2,4- or 2,5-dichloroaniline or aniline-3-trimethylammonium chloride is used, orange-coloured dyestuffs are obtained (Index No. 5-6). The diazo components 4-methoxyaniline, 2-methoxyaniline, 4-ethoxyaniline (Index No. 8), 2-(4-aminophenyl)-6-methylbenzothiazole, 2-(4-aminophenyl)-4,6-dimethylbenzothiazole, 2-(4-aminophenyl)-benzimidazole (Index No. 7) or 2-aminonaphthalene-5-methylenetrimethylammonium chloride (Index No. 7) lead to dye-stuffs which colour paper in intense red hues. If the diazo components 4-aminoazobenzene or 2-methyl-4-aminoazobenzene or 2'-methoxy-4-aminoazobenzene or 4-aminoazobenzene-4'-trimethylammonium chloride or 2-methyl-4-aminobenzeneazo-2'-naphthalene-5-methylenetrimethylammonium chloride are used, disazo dyestuffs are obtained which colour paper in bluish-tinged red hues (Index No. 10).

If the bis-diazo component 4,4'-diaminobenzoylanilide is used as the diazo component, a red dyestuff is produced (Index No. 9).

The use of the coupling components 1,2, 1,12, 1,13, 1,14, 1,30 or 1,31 produces, together with the above diazo components, dyestuffs which have hues similar to those described above which were obtained with the coupling component 1,1.

We claim:

1. A triazine compound which in its betaine form corresponds to the formula

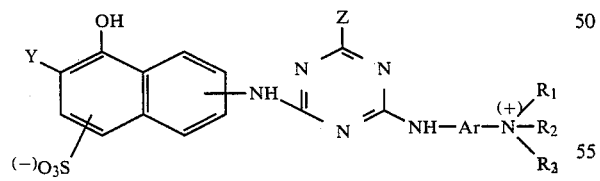

in which
Y is hydrogen or the radical of an azo dyestuff,
Ar is phenylene or phenylene substituted by halogen, $C_1$-$C_4$-alkyl or $C_1$-$C_4$-alkoxy,
Z is

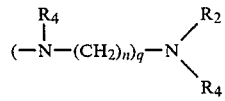

$R_1$, $R_2$ and $R_3$ are hydrogen, $C_1$- to $C_4$-alkyl or benzyl any of which is unsubstituted or substituted by hydroxyl, $C_1$- to $C_4$-alkoxy, halogen or cyano, or benzyl also substituted by $C_1$-$C_4$-alkyl,
$R_4$ is $R_3$ or phenyl which is unsubstituted or substituted by halogen, $C_1$-$C_4$-alkyl, $C_1$-$C_4$-alkoxy or

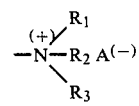

$A^{(-)}$ is an anion,
n is 2 or 3 and q is 0, 1 or 2, and the molecule contains at least one basic or cationic group more than sulfonic acid groups.

2. A triazine compound according to claim 1, in which
Y is hydrogen.

3. A triazine compound according to claim 1, in which
Y is hydrogen,
Z is aminoethylpiperazine and

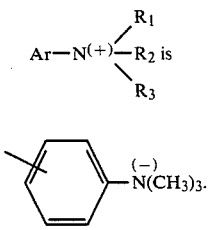

4. A triazine compound according to claim 1, of the formula

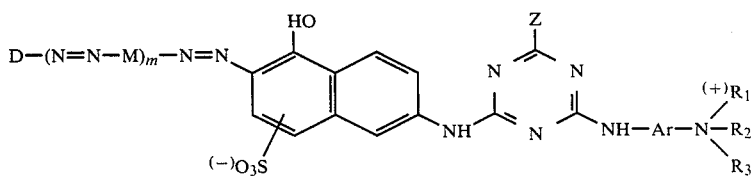

wherein
D and M are benzene or naphthalene any of which is unsubstituted or substituted by $C_1$-$C_4$-alkoxy, $C_1$-$C_4$-alkyl, halogen, a sulphonic acid group, —NH—COCH$_3$ or —NH—CO—C$_6$H$_5$,

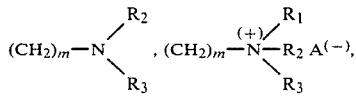

m is 0 or 1,

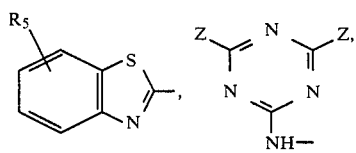

$R_5$ is hydrogen, methyl, methoxy or halogen, and the molecule contains at least one of basic or cationic groups more than sulfonic acid groups.

5. A triazine compound according to claim 1, of the formula

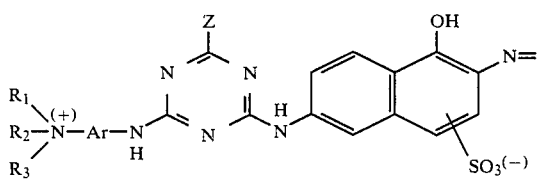 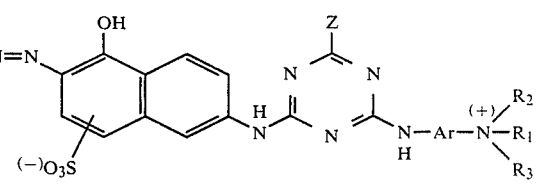

wherein
A is the radical of an aromatic tetraazo component, and the total number of basic and cationic groups is larger than the number of sulphonic acid groups.

6. A triazine compound according to claim 5, in which
A is 1,4- or 1,3-phenylene, either of which is unsubstituted or substituted by $C_1$-$C_4$-alkyl, hydroxyl, $C_1$-$C_4$-alkoxy or halogen, or is

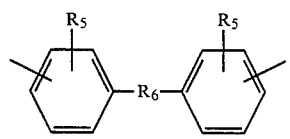

$R_5$ is hydrogen, methyl, methoxy or halogen,
$R_6$ is a direct bond, —(CH$_2$)$_p$—, —O—, —O—(CH$_2$)$_p$—O—, —SO$_2$—, —NH—CO—, —NH—CO—NH—, —NH—CO—(CH$_2$)$_p$—CO—NH—, —CO—NH—(CH$_2$)$_p$—NH—CO— or

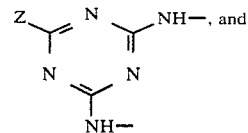

p is 1, 2 or 3.

7. A triazine compound according to claim 4 wherein Z is aminoethylpiperazine and

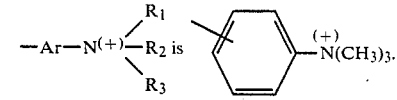

8. A triazine compound according to claim 5 wherein Z is aminoethylpiperazine and

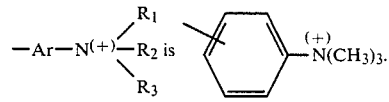

9. A triazine compound according to claim 4, of the formula:

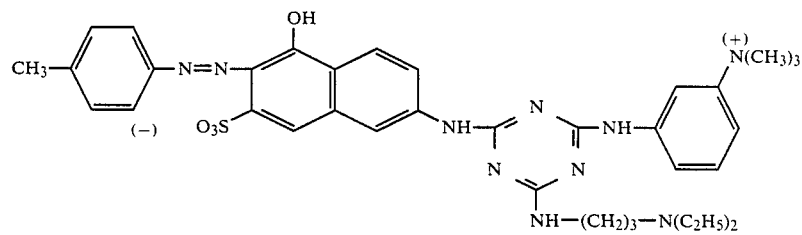

10. A triazine compound according to claim 4, of the formula:

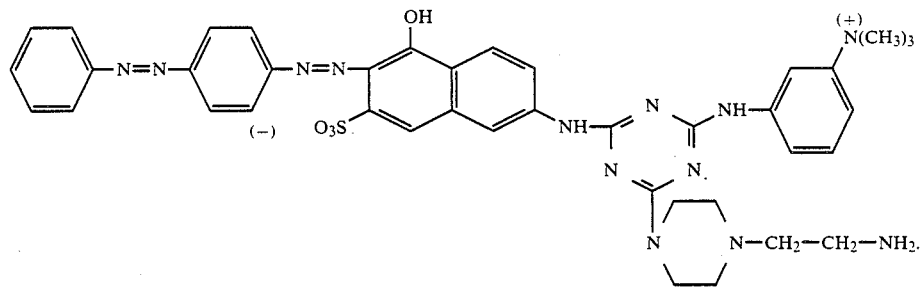
11. A triazine compound according to claim 4 of the formula:
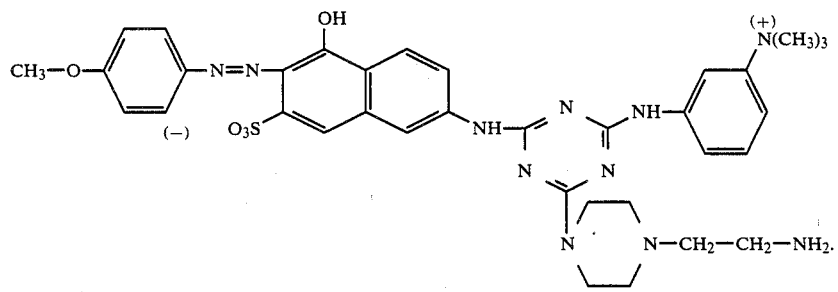
12. A triazine compound according to claim 4, of the formula:
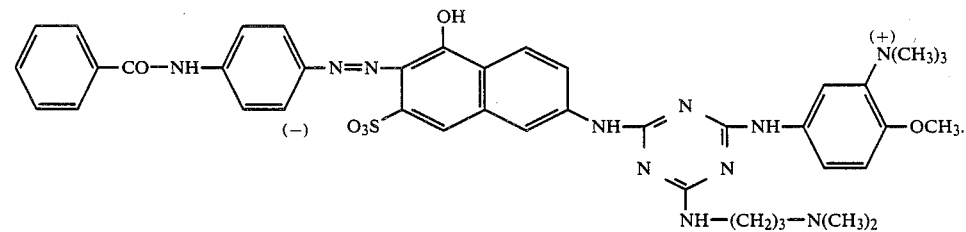
13. A triazine compound according to claim 4 of the formula:
14. A triazine compound according to claim 4 of the formula:
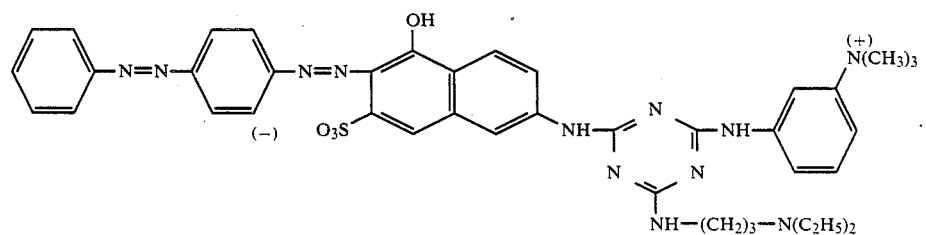
15. A triazine compound according to claim 4 of the formula:

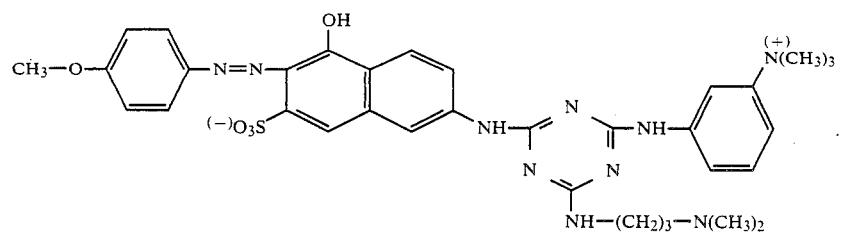
16. A triazine compound according to claim 1, wherein in the radical
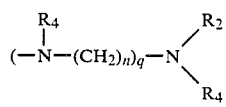
$R^2$ and $R^4$ are connected to form piperdine, morpholine or piperazine.
* * * * *